United States Patent [19]
Kelley

[11] Patent Number: 5,415,622
[45] Date of Patent: May 16, 1995

[54] EASILY REMOVED TUBULAR CAST ASSEMBLY AND METHOD FOR REMOVING A CAST

[75] Inventor: Ronald L. Kelley, Huntersville, N.C.

[73] Assignee: Parker Medical Associates, Charlotte, N.C.

[21] Appl. No.: 171,233

[22] Filed: Dec. 21, 1993

Related U.S. Application Data

[60] Division of Ser. No. 92,394, Jul. 15, 1993, which is a continuation-in-part of Ser. No. 474,527, Feb. 2, 1990, abandoned.

[51] Int. Cl.⁶ ................................................ A61F 5/00
[52] U.S. Cl. ................................................. 602/5; 602/8
[58] Field of Search ........................................ 602/5–12, 602/60–66, 76

[56] References Cited

U.S. PATENT DOCUMENTS

| | | | |
|---|---|---|---|
| 2,103,942 | 12/1937 | Gillin | 128/91 |
| 2,169,203 | 8/1939 | Hinchliff | 602/62 |
| 2,267,070 | 12/1941 | Baldwin | 602/62 |
| 2,480,849 | 9/1949 | Gersh et al. | 128/91 |
| 2,512,081 | 6/1950 | Young | 18/5 |
| 2,761,443 | 9/1956 | Parker | 128/91 |
| 3,085,569 | 4/1963 | Cook et al. | 128/91 |
| 3,631,855 | 1/1972 | Fehlau | 602/12 |
| 3,683,903 | 8/1972 | Fox et al. | 128/90 |
| 4,019,506 | 4/1977 | Eschmann | 602/9 |
| 4,041,941 | 8/1977 | Driver | 602/9 |
| 4,188,943 | 2/1980 | Sjöstrand | 128/91 A |
| 4,411,262 | 10/1983 | von Bonin et al. | 128/90 |
| 4,454,874 | 6/1984 | Monnier | 128/91 R |
| 4,770,299 | 9/1988 | Parker | 206/409 |
| 4,869,046 | 9/1989 | Parker | 53/416 |
| 4,899,738 | 2/1990 | Parker | 128/90 |
| 4,989,593 | 2/1991 | Campagna | 602/8 |
| 5,003,970 | 4/1991 | Parker et al. | 128/90 |
| 5,016,622 | 5/1991 | Norvell | 602/7 |
| 5,027,803 | 7/1991 | Scholz | 602/8 |

FOREIGN PATENT DOCUMENTS

2055582  3/1981  United Kingdom.

*Primary Examiner*—Michael A. Brown
*Attorney, Agent, or Firm*—W. Thad Adams, III

[57] ABSTRACT

A tubular cast product having an outer container formed of moisture-impervious material. A cast tube that is placed on and surrounds a body part. The cast tube includes a reactive system impregnated into or coated onto the tube. The cast tube also includes a narrow weakness zone along it length.

11 Claims, 7 Drawing Sheets

EASILY REMOVED TUBULAR CAST ASSEMBLY AND METHOD FOR REMOVING A CAST

TECHNICAL FIELD AND BACKGROUND OF THE INVENTION

This application is a divisional of application Ser. No. 08/092,394, filed on Jul. 15, 1993, which is a continuation-in-part of U.S. Ser. No. 07/474,527, filed Feb. 2, 1990, now abandoned.

The present invention relates generally to the field of orthopedic medicine and more specifically to an improved cast formed of a tubular fabric structure impregnated or coated with a moisture-curable plastic material, a tubular cast assembly which includes the tubular cast and its packaging, a method for constructing such an improved tubular cast assembly and a method for applying a cast to a body part to be immobilized. The product includes structural features which permit the cast to be easily removed without the use of a cast saw when immobilization of the limb is no longer required or the cast needs to be changed.

Medical bandages for use in the treatment of injuries, such as broken bones requiring immobilization of a body member, are generally formed from a long strip or strips of fabric or scrim material, referred to as cast tape, impregnated with a substance which hardens into a rigid structure after the strip or strips have been wrapped around the body member. The hardening substances traditionally used in carrying out this procedure are plaster-of-paris and polyurethanes.

Conventional practice, which is still very common, has been to fabricate a cast or splint upon an injured limb by initially applying to the limb a protective covering of a cotton fabric or the like and then overwrapping the covering and the underlying body part with a woven cloth impregnated with plaster-of-paris or polyurethane which has been wetted by dipping in water immediately prior to application. This practice is still in widespread use but possesses several significant disadvantages.

The above-described application procedure is messy and time consuming. Several components are required and considerable skill is necessary. If too little cast tape is used to fabricate the plaster cast, breaking or "hinging" at stress points can occur as the patient wears the cast over a period of time. This, of course, requires replacement of the cast. It is common to make a plaster cast heavier than it really needs to be in order to insure against breaking. This practice creates its own problems, including greater weight for the patient to carry, greater heat and moisture retention and greater use of materials.

In order to alleviate these disadvantages of the conventional application procedure for plaster-of-paris casts and splints, unitary splinting materials have been devised and are disclosed in, for example, U.S. Pat. Nos. 3,900,024, 3,923,049, and 4,235,228. All of these patents describe a padding material with a plurality of layers of plaster-of-paris impregnated cloth. Such unitary splinting materials are not as messy and can be applied more quickly but still suffer from a number of disadvantages inherent in plaster-of-paris cast materials. All plaster-of-paris splints have a relatively low strength to weight ratio which results in a finished splint which is very heavy and bulky. Plaster-of-paris splints are slow to harden, requiring 24 to 72 hours to reach maximum strength. Since plaster-of-paris breaks down in water, bathing and showering are difficult. Even if wetting due to these causes can be avoided, perspiration over an extended period of time can break down the plaster-of-paris and create a significant problem with odor and itching.

A different way of forming a cast is disclosed in U.S. Pat. Nos. 4,411,262 and 4,502,479. The casting materials disclosed in these patents comprise a flexible fabric impregnated with a moisture-curing resin. The impregnated fabric is enclosed in a moisture-free, moisture-impervious package where it is stored until immediately prior to use. Compared to plaster-of-paris, these products are extremely lightweight, have a very high strength-to-weight ratio and can be made relatively porous, permitting a flow of air through the casting material. Prior art moisture-curing systems include a package within which is contained a plurality of layers of fabric, such as fiberglass, impregnated with a moisture-curing resin. The layers of fabric are applied in layers much as with plaster coated strips. Judgment and experience is required to apply the layers of fabric in manner which results in a cast which will securely immobilize the body part, provide greater strength in those areas of the cast where necessary, and yet will be as light weight as practical in order that the patient can safely wear the cast for an extended time.

From the above discussion, both the conventional plaster-of-paris casting method and the more recent moisture-curable resin casting method possess both advantages and disadvantages. On the one hand, plaster-of-paris casts are bulky, heavy and difficult to apply whereas moisture-curable resin casts are lightweight, durable and relatively easy to apply. On the other hand, plaster-of-paris can be very easily stored and used as needed since it has a relatively long shelf life so long as it is not completely wetted, whereas the moisture-curable resins are very sensitive to the presence of even minute amounts of moisture. This requires that either the materials be packaged in a wide variety of different shapes and sizes or unused portions be discarded, generating a substantial amount of waste and increasing the effective cost of the product. This invention combines the advantages of both plaster-of-paris and moisture-curable resin systems while avoiding their respective disadvantages by providing a tubular cast which is already formed and ready to place on the body part, and which is easily applied and removed.

In addition, the invention described below allows various parts of the cast to provide different degrees of strength. For example, a portion of the cast to be positioned around the smaller body part, such as the ankle or wrist, will preferably be stronger than elsewhere in accordance with good medical practice.

As used in this application unless otherwise explained by context, the terms "cast" and "tubular cast assembly" refer to the finished structure as it exists on the body part to be immobilized. The term "cast tube" refers to the outer tube which is treated with a moisture-curable reactive system and then placed over a previously applied sleeve. The term "tubular cast product" refers to the cast tube and the moisture impervious packaging within which the cast tube is stored until just before use.

Tubular casts are known in the prior art. However, whether formed into a tube on the limb by applying numerous strips of material, or pre-formed and slipped onto the limb in tubular form, the cast must still be removed using a cast saw. A cast saw has a serrated blade which looks to the patient as if it is rotating in the manner of a circular saw. Many patients, particularly children, become frightened at the prospect of their cast being removed by the saw. In fact, the cast saw blade is not particularly sharp, and the blade oscillates with a short periodicity so that there is little danger of the patient being injured. However, the apparent danger of the saw, particularly the noise of the saw, outweighs the reality of the safety of the saw in the minds of many patients.

Cast saws have other disadvantages as well. They are noisy, require maintenance and, of course, as subject to damage, wear and blade replacement. Removal of a cast with a cast saw generates airborne fiberglass and/or plaster dust which is messy and is sometimes perceived as hazardous products. The cast according to this invention may be removed with or without a cast saw.

SUMMARY OF THE INVENTION

It is therefore an object of the invention to provide a cast tube impregnated or coated with a moisture-curable resin which hardens the cast tube material upon exposure to moisture to form a rigid, self-supporting cast, and which is easy to remove.

It is another object of the invention to provide a cast tube which can be removed without the use of a cast saw.

It is another object of the invention to provide a cast which is pre-constructed and ready to apply to a body part to be immobilized.

It is another object of the invention to provide a cast which uses a moisture curable resin to harden the cast and which is packaged and ready to apply.

It is another object of the invention to provide a method of constructing a tubular cast product which includes structural features which permit easy removal of the cast from the body part.

It is another object of the invention to provide a method of applying a tubular cast assembly to a body part to be immobilized.

It is another object of the invention to provide a cast which is preconstructed for application to a particular body part such as the foot and lower leg or the hand, wrist and forearm.

These and other objects of the present invention are achieved in the preferred embodiments disclosed below by providing a tubular cast assembly for immobilizing a body part, such as a limb, comprising an undercast protective sleeve for being placed on the body part and a cast tube for being placed on and surrounding the body part over the undercast protective sleeve. The undercast protective sleeve protects the body part against contact with the skin by the cast tube. The cast tube comprises a fabric tube of a size suitable for the body part to be immobilized and a reactive system impregnated into or coated onto the fabric tube. The system remains stable when maintained in substantially moisture-free conditions and hardens upon exposure to sufficient moisture to form a rigid, light-weight, self supporting tubular structure. Adjacent edges of the fabric tube along the length of the tube define a narrow weakness zone therebetween to serve as a line along which the tube is severed along the length thereof in preparation for removal.

According to one preferred embodiment of the invention, the fabric tube is knitted, and the weakness zone comprises a knit construction of reduced density and strength which is easily severable along the length thereof.

According to another preferred embodiment of the invention, the fabric tube is knitted, and the weakness zone comprises a slit into which is secured a narrow width of easily severable material.

According to yet another preferred embodiment of the invention, the fabric tube is knitted, and the weakness zone comprises a slit, and eyelets are attached to and extend along the length of the fabric tube for being interconnected together by a laced cord to thereby hold the edges of the fabric tube adjacent the slit together.

According to one preferred embodiment of the invention, the fabric tube comprises a knitted sock for being placed over the foot, ankle and lower leg.

According to yet another preferred embodiment of the invention, the knit construction in the weakness zone includes a reduced number of threads in relation to the construction of the fabric tube.

According to yet another preferred embodiment of the invention, the knit construction in the weakness zone comprises a knit construction having a substantially lower stitch density in relation to the construction of the fabric tube.

According to yet another preferred embodiment of the invention, the easily severable material in the weakness zone comprises a relatively thin fabric chosen from the group consisting of a thin, relatively weak fabric woven from relatively fine yarns which are easy to sever; a thin, relatively weak knitted fabric knitted from relatively fine yarns which are easy to sever, and an open mesh fabric formed of a relatively small number of relatively large yarns.

According to yet another preferred embodiment of the invention, the cast tube comprises a tube constructed in a shape for being placed over the hand, wrist and forearm of a wearer.

According to yet another preferred embodiment of the invention, the knitted cast tube includes an open toe and a knit-in heel pocket and is sized for placement on the foot and calf.

Preferably, the cast tube comprises knitted fiberglass.

According to one preferred embodiment of the invention, cast tube includes a reenforced heel pocket.

According to another preferred embodiment of the invention, cast tube includes a reenforced ankle.

According to yet another preferred embodiment of the invention, the cast tube comprises a tube suitable for placement over the hand, wrist and forearm and includes a hole positioned for receiving a thumb therethrough.

According to one preferred embodiment of the invention, the cast product comprises an outer container formed of moisture-impervious material and a cast tube for being placed on and surrounding the body part over an undercast protective sleeve placed on the body part to prevent contact between the cast tube and the skin. The cast tube is positioned in the outer container in substantially moisture-free conditions and sealed therein against entry of moisture until use. The cast tube includes a reactive system impregnated into or coated onto the cast tube. The system remains stable when maintained in substantially moisture-free conditions and hardens upon exposure to sufficient moisture to form a rigid, light-weight, self supporting structure. The cast tube includes adjacent edges along the length of the tube defining a narrow weakness zone therebetween to serve as a line along which the tube is severed along the length thereof in preparation for removal.

According to one preferred embodiment of the invention, the fabric tube is knitted, and wherein the weakness zone comprises a knit construction of reduced density and strength which is easily severable along the length thereof.

According to another preferred embodiment of the invention, the fabric tube is knitted, and the weakness zone comprises a slit into which is secured a narrow width of easily severable material.

According to yet another preferred embodiment of the invention, the fabric tube is knitted, and the weakness zone comprises a slit. Eyelets are attached to and extend along the length of the fabric tube for being interconnected together by a laced cord to thereby hold the edges of the fabric tube adjacent the slit together.

According to yet another preferred embodiment of the invention, the knitted tube includes an open toe and a knit-in heel pocket and is sized for placement on the foot and calf.

According to yet another preferred embodiment of the invention, the cast tube comprises knitted fiberglass.

According to yet another preferred embodiment of the invention, the cast tube includes a reenforced heel pocket.

According to yet another preferred embodiment of the invention, the cast tube includes a reenforced ankle.

According to yet another preferred embodiment of the invention, the cast tube comprises a tube of a size suitable for placement over the hand, wrist and forearm and includes a hole positioned in the cast tube for receiving a thumb therethrough.

An embodiment of the method of removing a cast according to the invention comprises the steps of applying a undercast protective sleeve to the body part to be immobilized and providing a fabric tube of a size suitable for the body part to be immobilized. A reactive system is impregnated into or coated onto the fabric tube. The system remains stable when maintained in substantially moisture-free conditions and hardens upon exposure to sufficient moisture to form a rigid, light-weight self supporting tubular structure. The adjacent edges of the fabric tube along the length of the tube define a narrow weakness zone therebetween to serve as a line along which the tube is severed along the length thereof in preparation for removal.

The cast tube is removed from an outer container formed of moisture-impervious material in which the cast tube has been sealed in substantially moisture-free conditions against entry of moisture until use. The cast tube has a reactive system impregnated into or coated onto the cast tube, the system remaining stable when maintained in substantially moisture-free conditions and hardening upon exposure to sufficient moisture to form a rigid, light-weight, self supporting structure. The cast tube is wet, and the wetted cast tube is placed on and surrounding the body part over the undercast protective sleeve. The undercast protective sleeve protects the body part against contact with the skin by the cast tube. The cast tube is allowed to harden. At a medically appropriate time, the cast is removed by severing the cast along the weakness zone.

According to one preferred embodiment of the invention, the weakness zone includes two zone segments extending along opposite sides of the fabric tube, and the method includes the step of severing the fabric tube along both weakness zone segments thereby permitting the cast to be separated into two separate halves.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
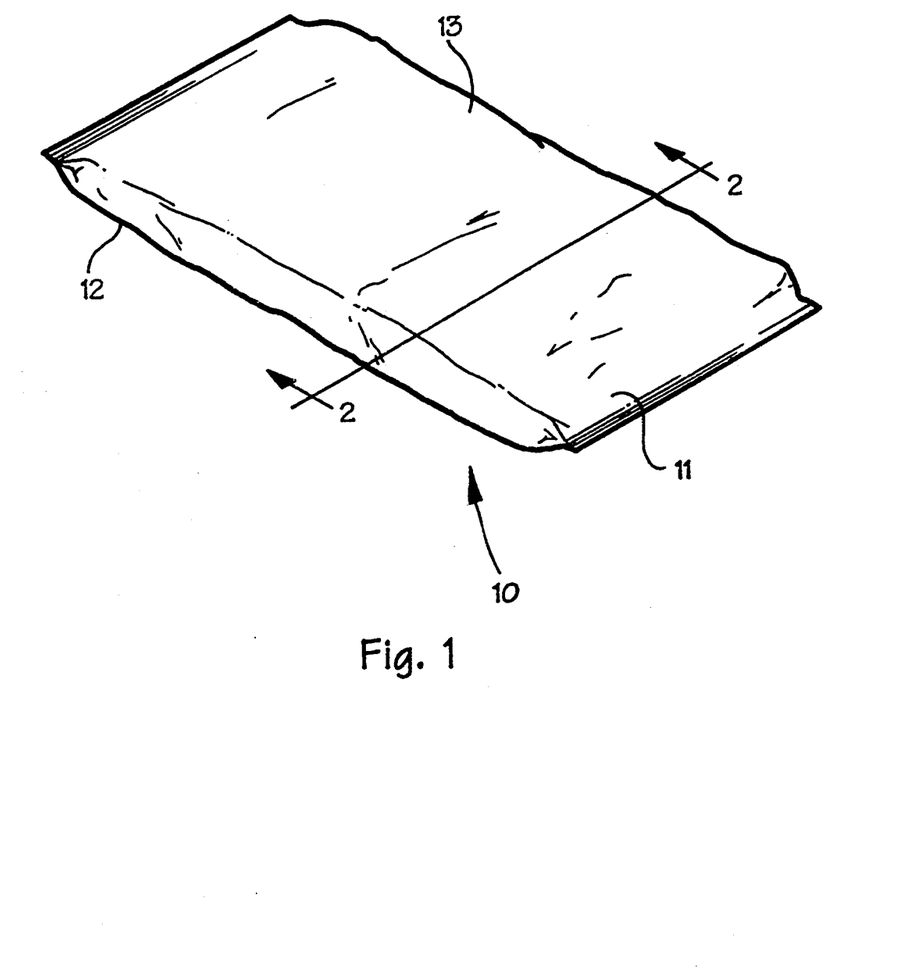
FIG. 1 is a illustrates the water-proof package within which the cast product according to the invention is packaged.

Referring now specifically to the drawings, a cast tube product according to the present invention is illustrated in FIG. 1 and shown generally at reference numeral 10. Cast tube product 10 includes a package 11 formed of two laminated sheets 12, 13 placed in registration and heat sealed along their opposite sides to form a pouch. The laminated sheets 12, 13 are each formed of three layers. The outer layer is formed of a tear-resistant plastic film. The middle layer comprises aluminum foil and acts as a moisture barrier. The inner layer is a plastic film having thermoplastic properties suitable for heat sealing the interior of package 11 securely against moisture.

Figure 2:
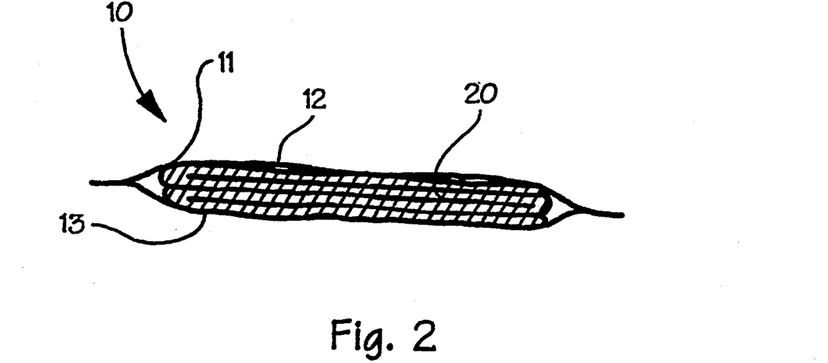
FIG. 2 is a cross-section taken along lines 2—2 of FIG. 1.

As is shown in FIG. 2, the cast tube product 10 includes a cast tube 20 folded or rolled on itself and sealed into the package 11 with as little air space left in the package as practicable. Rolling of the cast tube 20, is preferable, since this facilitates placement of the cast tube onto the body part. As described in further detail below, cast tube 20 is rib knitted of fiberglass yarn and produces a relatively heavy tube. The cast tube 20 can be sized in both length and diameter to fit over either a foot, ankle and lower leg, or over a hand, wrist and forearm. An exemplary specification for the yarn and knitted fabric is set out below:

| Machine type | AMY 301 |
| --- | --- |
| Cylinder size | 3¾ inches diameter |
| Needles | 108 |
| Wales/inch | 9 plus or minus 1 |
| Courses/inch | 9 plus or minus 1 |
| Materials | |
| Fiberglass | ECDE 37 1/0 LFX or 401 |
| Spandex | 310 denier type 128C Lycra or 560 denier cleerspan |
| Nylon | 2/70 denier |

Two ends of ECDE 75 1/0 fiberglass yarn and one end of 2/70 nylon yarn are knitted over the cushion sinker nibs utilizing two fingers. One end of 560 denier cleerspan spandex yarn is knitted on alternate needles utilizing every other needle. In the knitting process 98 wales (98 needles) are knitted and 10 wales (10 needles) are skipped. One hundred and eight sinkers and 98 needles are used in knitting the fiberglass and nylon yarns, and 108 sinkers and 49 needles are utilized in knitting the cleerspan nylon.

Of course, many variations are possible to take into account differing product requirements.

Figure 3:
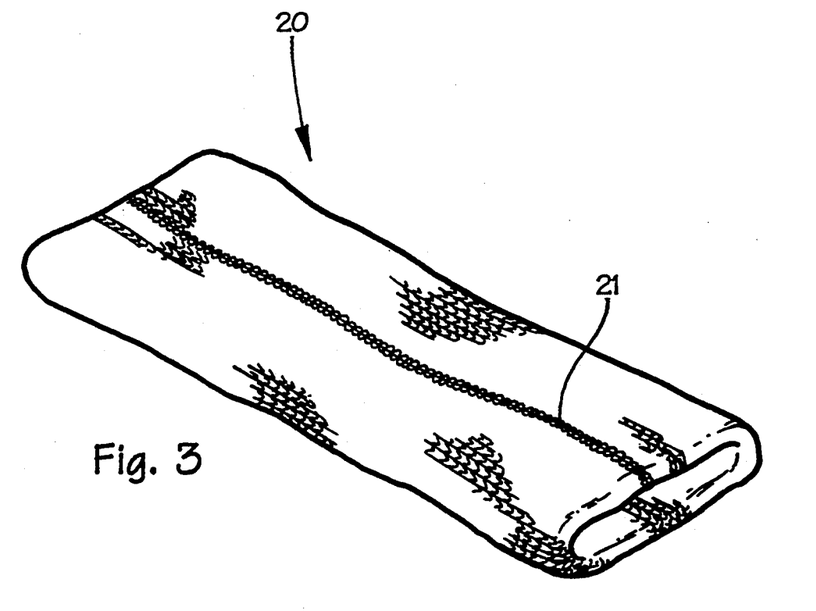
FIG. 3 is a cast tube formed as a straight knitted tube.

The cast tube 20 intended for use on a hand, wrist and forearm is shown in FIG. 3. The cast tube 20 is knitted as described above and is sized to snugly encircle the hand, wrist and forearm. A weakness zone 21 is formed along the longitudinal extent of the cast tube 20 by dropping needles in the zone as knitting progresses. The line thus formed, having fewer threads, is substantially easier to cut with a pair of scissors when the cast tube 20 is ready to remove, but does not effect in any way the performance of the cast tube 20 during the time it is worn. In fact, the weakness zone is scarcely noticeable in use, but is exaggerated in the drawing for purposes of clarity.

Figure 4:
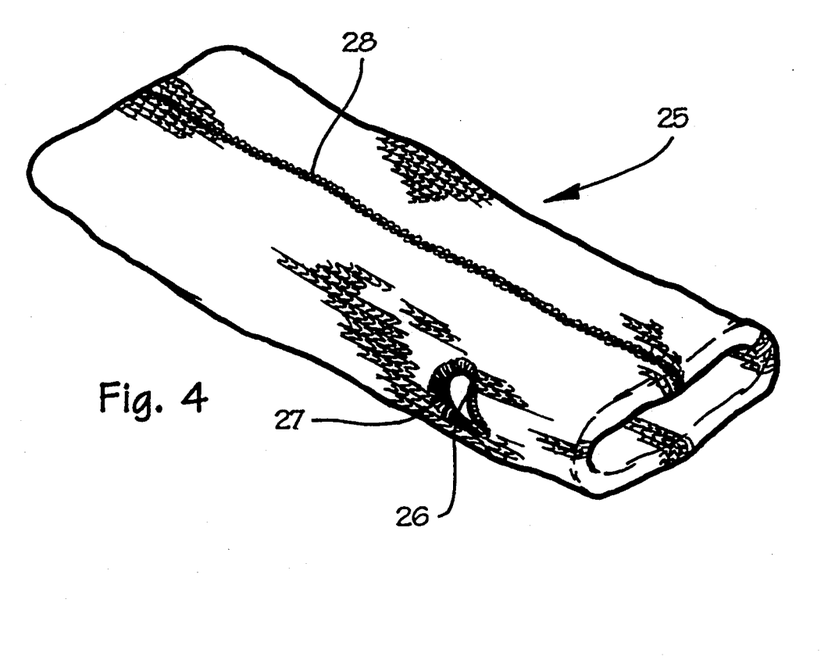
FIG. 4 is a cast tube with a hole formed for a thumb.

The cast tube 20 shown in FIG. 3 does not include a thumb hole. As is shown in FIG. 4, a variant cast tube 25 includes a thumb hole 26, which permits the cast tube 25 to be easily positioned further onto the hand. The edge of the cast tube 25 forming the thumb hole 26 is serged with overedge sewing stitches 27 to prevent unraveling. The weakness zone is shown at 28.

Figure 5:
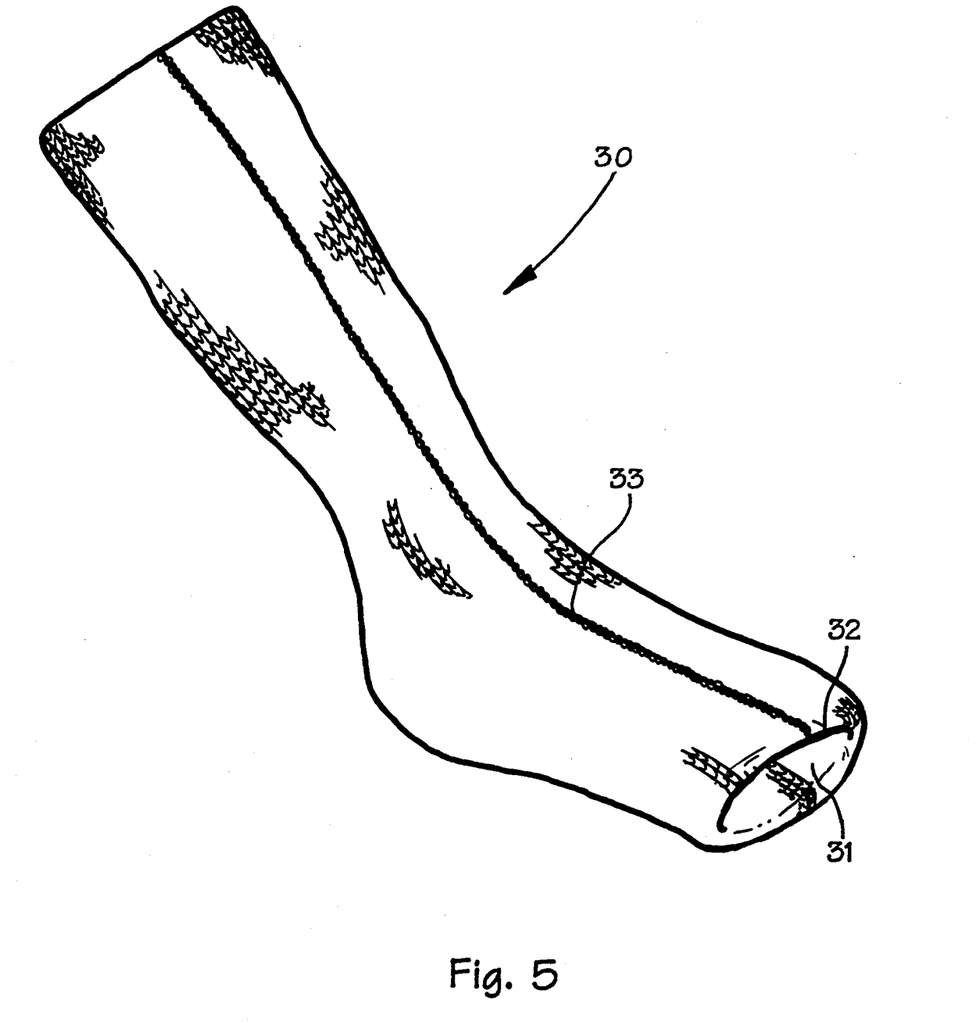
FIG. 5 is a knitted cast tube in the form of a sock with an open toe.

Referring now to FIG. 5, a cast tube 30 intended for use on a foot, ankle, and lower leg is illustrated. Cast tube 30 is knitted in the form of a sock, and in the embodiment shown in FIG. 5, the toe is then cut out to form a toe opening 31 and serged with stitches 32 to prevent unraveling.

A weakness zone 33 is formed along the longitudinal extent of the cast tube 30 by dropping needles in the zone as knitting progresses. The weakness zone 33 thus formed, having fewer threads, is substantially easier to cut with a pair of scissors when the cast tube 30 is ready to remove, but does not effect in any way the performance of the cast tube 30 during the time it is worn. In fact, the weakness zone 33 is scarcely noticeable in use, but is exaggerated in the drawing for purposes of clarity.

The cast tubes 10, 20 and 30 are impregnated or coated with a reactive system which remains stable when maintained in substantially moisture-free conditions but which hardens upon exposure to sufficient moisture to form a rigid, self-supporting structure. A typical formulation of the reaction system is set forth in the following table:

| Typical Formulation: | | | |
|---|---|---|---|
| Isonate ↓ 143L | or | | |
| Mondur ↓ CD | or | polyisocyanate | 50.0% |
| Rubinate ↓ XI168 | | | |
| Pluracol ↓ P1010 | | polyol | 46.6% |
| DC-200 Silicone | | defoaming agent | 0.30% |
| Benzoyl Chloride | | stabilizer | 0.10% |
| Thancat ↓ DM-70 | | catalyst | 3.0% |
| | | | 100% |

A complete discussion of the parameters of the reactive system, the manner of production and the variables which apply are found in U.S. Pat. No. 4,411,262, referred to above.

Figure 6:
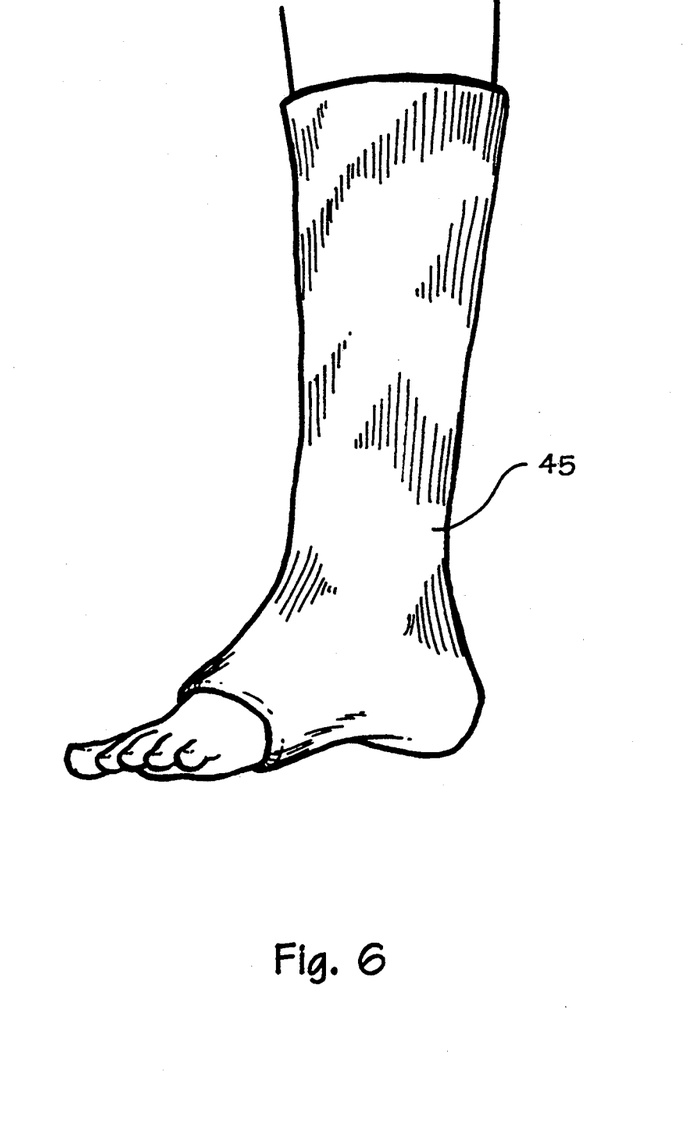
FIG. 6 is a perspective view of the undercast protective sleeve in the form of a sock with an open toe.

Referring now to FIG. 6, the tubular cast assembly is constructed by first applying a undercast protective sleeve 45 to the foot, ankle and lower leg. Sleeve 45 ordinarily comprises one or two layers of a typical elastic "stockinette" material. Sleeve 45 may be formed by wrapping the foot, ankle and leg with overlapping layers of the stockinette, or as is shown in FIG. 6, applying a heavy duty fracture sock with an open toe to the body part. Alternatively, a closed toe sock can be used and, if desired, the toe is then cut out of the sock. When properly applied, the sleeve 45 appears as is shown in FIG. 6.

Then, a cast tube 30 is removed from package 11. The cast tube 30 is dipped in water for three or four seconds and excess water removed. Alternatively, moisture-curing can take place over a longer period of time by allowing contact between the cast tube 30 and atmospheric moisture.

The cast tube 30 is preferably rolled on itself into a tight ball. Cast tube 30 is applied by placing the open toe of cast tube 30 over the toes and onto the middle part of the foot, taking care to leave two or three inches of the undercast protective sleeve 45 exposed. When properly placed, the cast tube 30 is unrolled progressively up the foot, over the heel, up past the ankle and onto the lower leg. At the top of the cast tube 30 care should again be taken to leave two or three inches of the undercast protective sleeve 45 exposed. After any necessary smoothing and adjustment to remove wrinkles or twists, the exposed parts of the undercast protective sleeve 45 are folded over the adjacent edges of the cast tube 30 to form a protective barrier against the hardened cast tube 30.

Figure 7:
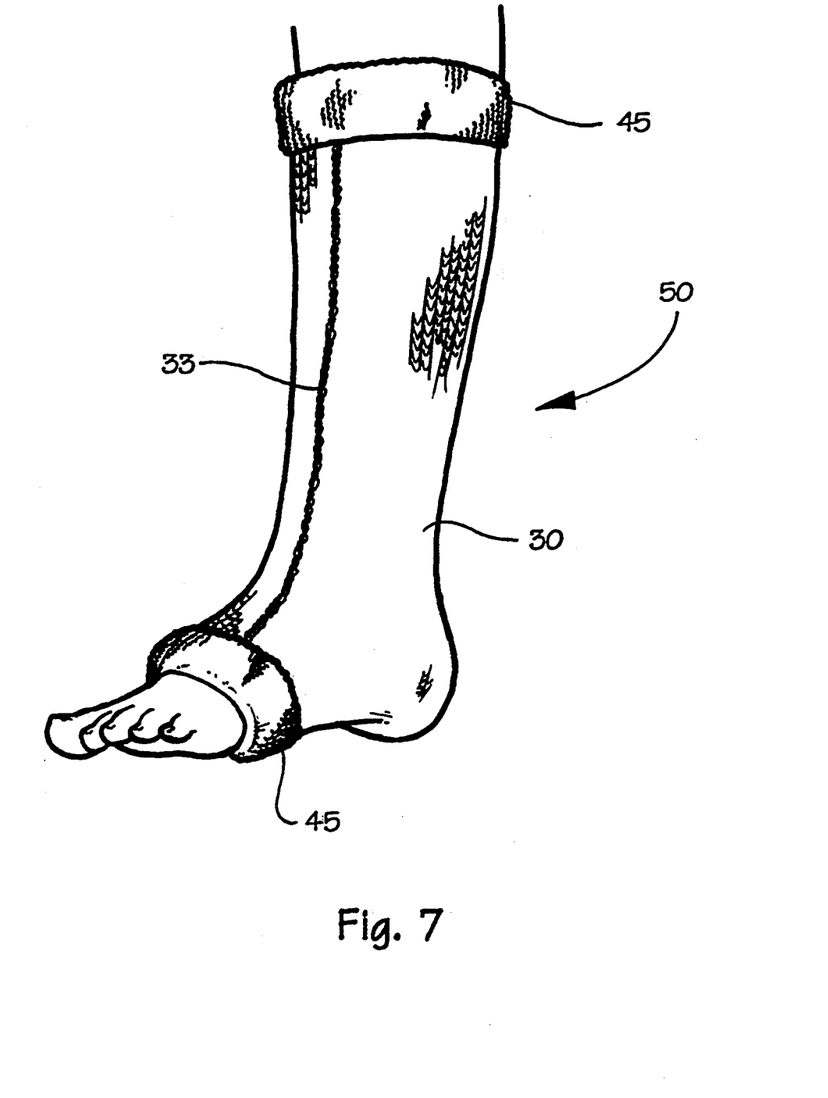
FIG. 7 is a view of a tubular cast constructed and applied according to an embodiment of the invention.

The finished product is shown in FIG. 7, and comprises a tubular cast assembly 50. Assembly 50 is durable yet light-weight, presents a smooth and finished appearance without the requirement of a skilled technician. The natural stretching of the knitted cast tube 30 as it conforms to the contours of the foot, ankle and leg creates relatively thin areas on the larger parts of the foot and leg, and relatively thicker areas on the narrow part of the ankle where the strength of the cast is therefore concentrated. This is a desirable characteristic of any cast but one which is very difficult to achieve in the prior art type of cast.

A similar effect is achieved when applying the cast tube 20 or 25 to the hand, wrist and forearm—the area across the wrist being thicker and therefore the strength of the cast being concentrated there.

The weakness zone 33 may be positioned at any point on the extent of the limb being immobilized. When the cast is ready to be removed, an ordinary pair of scissors is all that is required to cut through the threads defining the weakness zone 33. Then the protective sleeve 45 is separately removed.

Figure 8:
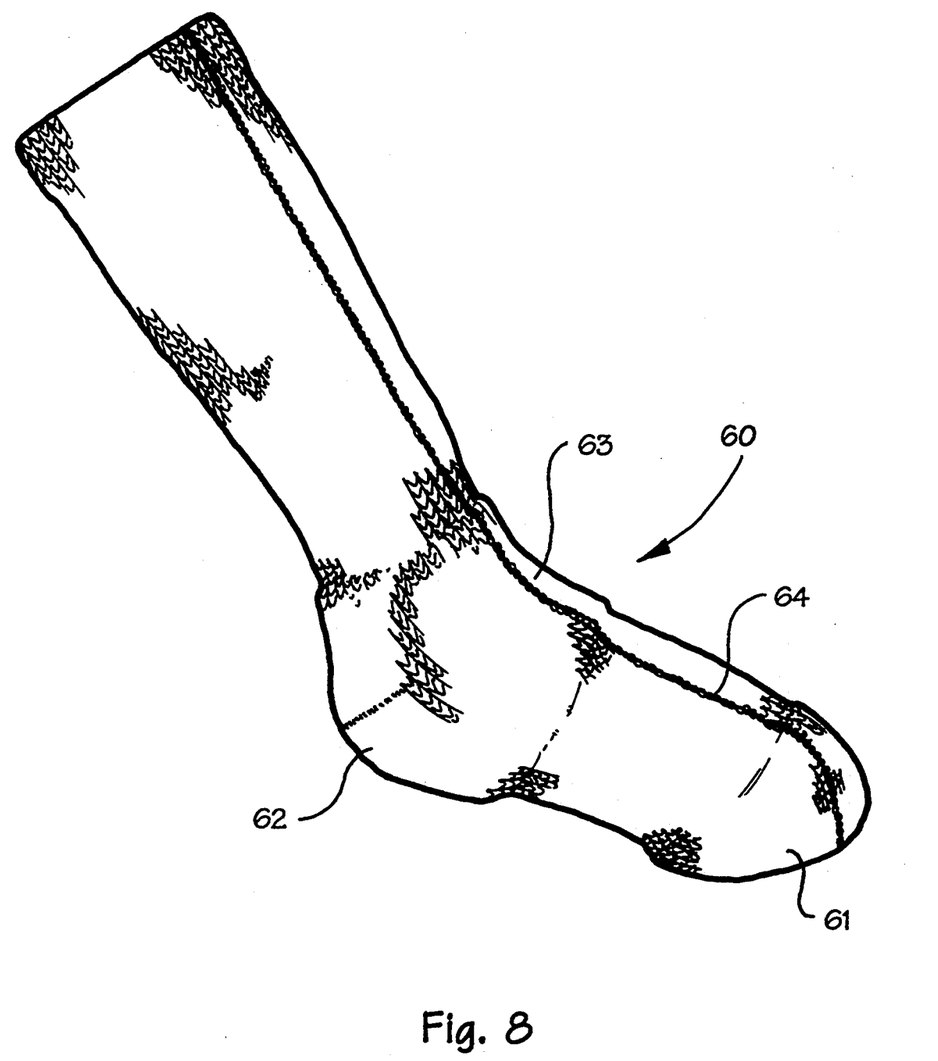
FIG. 8 is a cast tube with a closed toe and reenforced areas.

A further modified embodiment of a cast tube is shown in FIG. 8 and indicated at reference numeral 60. The cast tube 60 is formed as a sock, but is knitted with fiberglass yarn or some other similar hard, durable yarn. Of course, a sock intended for use as such would never be knitted of fiberglass or similar yarn since fiberglass cannot be worn next to the skin. Cast tube 60 has a closed toe 61, a knit-in heel pocket 62 and a reenforced zone 63 in the area of the heel. The reenforced area can be created by using conventional hosiery knitting techniques, such as laying in an extra yarn in the reenforced zone 63, or knitting using a doubled or heavier fiberglass yarn. The weakness area is at 64.

After application of the cast tube 60 as described above, the toe 61 is cut out. The advantage of leaving the toe 61 in the cast tube 60 until after application to the foot is that exactly the correct amount of the toe 61 can be removed so that the correct of amount of the previously-applied undercast protective sleeve 45 is left exposed for folding over the edge of the cast tube 60. It may be necessary to apply some adhesive tape to the raw, cut edge of the cast tube 60 to prevent ravelling.

Figure 9:
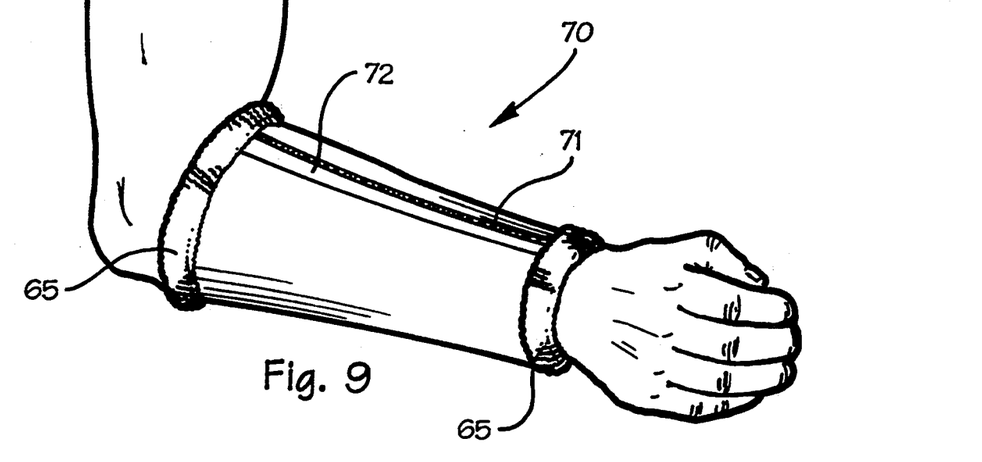
FIGS. 9, 10 and 11 are views of tubular casts constructed to permit different removal techniques.

A variation on the embodiment of FIG. 3 is shown in FIG. 9 in place on an arm. As with the foot cast shown in FIG. 7, a soft, protective sleeve 65 is first placed on the limb to be immobilized, being careful to leave sufficient overlap to permit turning the ends of the sleeve 65 over the raw edges of the cast tube 70. The weakness zone 71 is formed by slitting the cast tube 70 and piecing in a long strip of a relatively thin, lightweight fabric 72. The strip of fabric is secured to the cast tube 70 by sewing stitches or by a suitable form of adhesive bonding. To remove the cast, scissors are used to cut along the slit, severing the lightweight fabric 72 and permitting the cast to be removed from the limb.

Figure 10:
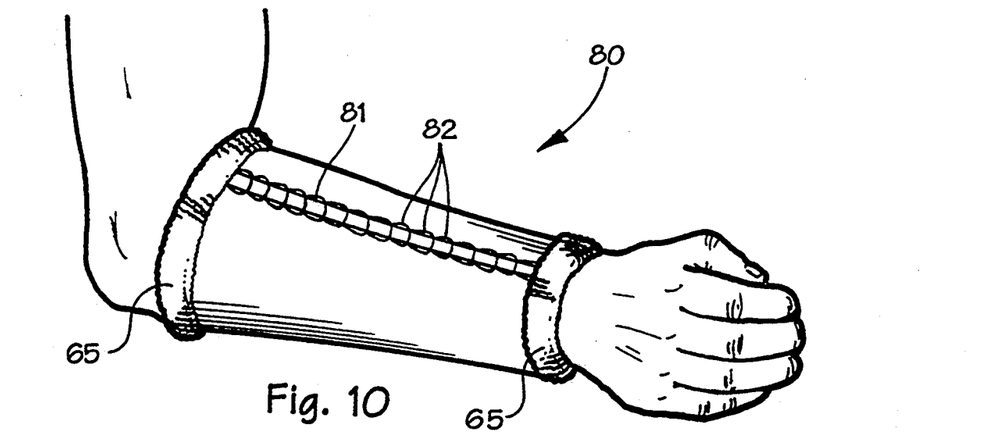

A further variation on the embodiment of FIG. 3 is shown in FIG. 10. The soft, protective sleeve 65 is first placed on the limb to be immobilized, being careful to leave sufficient overlap to permit turning the ends of the sleeve 65 over the raw edges of the cast tube 80. A weakness zone 81 is formed by slitting the cast tube 80 and then reconnecting edges of the cast tube 80 adjacent the slit by the use of a low density, loose, stitching, such as chain stitches 82. To remove the cast, scissors are used to cut along the chain stitches 82, severing the stitches 82 and permitting the cast 80 to be removed from the limb. Then, the protective sleeve 65 can be removed.

Figure 11:
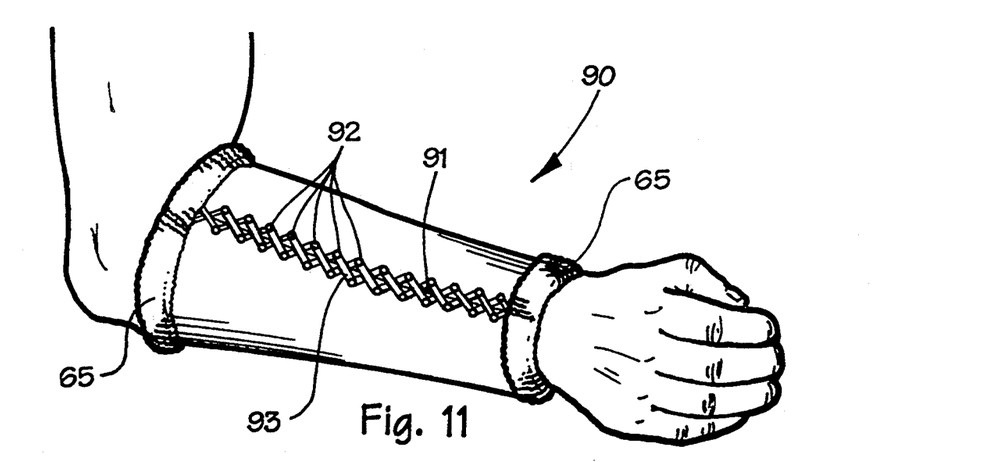

A further variation on the embodiment of FIG. 3 is shown in FIG. 11. The soft, protective sleeve 65 is first placed on the limb to be immobilized, being careful to leave sufficient overlap to permit turning the ends of the sleeve 65 over the raw edges of the cast tube 90. A weakness zone 81 is formed by slitting the cast tube 80 and then reconnecting edges of the cast tube 80 adjacent the slit by the use of mating lengths of eyelets 92 which are attached to the edges of the cast tube 90 adjacent the slit. The eyelets 92 are interconnected together by a laced cord 93 to thereby hold the edges of the cast tube 90 adjacent the slit together. To remove the cast, the lace is untied or cut and removed from the eyelets 92, permitting the cast 90 to be removed from the limb. Then, the protective sleeve 65 can be removed.

Of course, other ways of connecting the slit edges of the cast tubes together can also be used. In addition, pairs of opposing weakness zones can be constructed, so that when both are cut, the cast tube can be removed as two separate pieces, referred to as a "bivalve" removal. For example, two opposing zones of reduced thread size or number could be knitted into the cast tube. Cutting of the cast tube along both weakness zones essentially results in two separate cast pieces which are removed in a clamshell-like manner.

A cast tube is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A tubular cast product, comprising:
    (a) an outer container formed of moisture-impervious material; and
    (b) a cast tube for being placed on and surrounding the body part over an undercast protective sleeve placed on the body part to prevent contact between the cast tube and the skin, said cast tube positioned in said outer container in substantially moisture-free conditions and sealed therein against entry of moisture until use, said cast tube including a reactive system impregnated into or coated onto said fabric tube, said system remaining stable when maintained in substantially moisture-free conditions and hardening upon exposure to sufficient moisture to form a rigid, light-weight self supporting tubular structure, said cast tube including, said fabric tube incorporating along its length a narrow weakness zone, said fabric tube and said weakness zone together comprising a tubular structure to be extended completely around the immobilized body part for greater cast strength, durability and rigidity, said weakness zone comprising a material less dense than the material of the fabric tube and connecting adjacent edges of the fabric tube and providing an area along the length of the tube which may be easily severed and separated for removal of the cast.

2. A tubular cast assembly according to claim 1, wherein said fabric tube is knitted, and wherein said weakness zone comprises a knit construction of reduced density and strength which is easily severable along the length thereof.

3. A tubular cast product according to claim 2, wherein said knitted tube includes an open toe and a knit-in heel pocket and is sized for placement on the foot and calf.

4. A tubular cast product according to claim 2, wherein said cast tube comprises knitted fiberglass.

5. A tubular cast product according to claim 2, wherein said cast tube includes a reenforced heel pocket.

6. A tubular cast assembly according to claim 1, wherein said fabric tube is knitted, and wherein said weakness zone comprises a slit into which is secured a narrow width of easily severable material.

7. A tubular cast product according to claim 6, wherein said cast tube includes a reenforced ankle.

8. A tubular cast product according to claim 6, wherein said cast tube comprises a tube of a size suitable for placement over the hand, wrist and forearm and includes a hole positioned in said cast tube for receiving a thumb therethrough.

9. A tubular cast product according to claim 1, wherein said cast tube comprises a knitted tube.

10. A method of applying and removing a cast to a body part to be immobilized, comprising the steps of:
    (a) applying a undercast protective sleeve to the body part to be immobilized;
    (b) providing a fabric tube of a size suitable for the body part to be immobilized and having a reactive system impregnated into or coated onto said fabric tube, said reactive system remaining stable when maintained in substantially moisture-free conditions and hardening upon exposure to sufficient moisture to form a rigid, light-weight self supporting tubular structure; said fabric tube incorporating along its length a narrow weakness zone, said fabric tube and said weakness zone together comprising a tubular structure to be extended completely around the immobilized body part for greater cast strength, durability and rigidity, said weakness zone comprising a material less dense than the material of the fabric tube and connecting adjacent edges of the fabric tube and providing an area along the length of the tube which may be easily severed and separated for removal of the cast;

(c) removing the cast tube from an outer container formed of moisture-impervious material in which said cast tube has been sealed in substantially moisture-free conditions against entry of moisture until use;

(d) wetting the cast tube;

(e) placing the wetted cast tube on and surrounding the body part over the undercast protective sleeve, said undercast protective sleeve protecting the body part against contact with the skin by said cast tube;

(f) allowing the cast tube to harden; and (g) at a medically appropriate time, removing the cast by severing the cast along the weakness zone.

11. A method of applying a cast according to claim 10, wherein the weakness zone includes two zone segments extending along opposite sides of said fabric tube, and including the step of severing the fabric tube along both weakness zone segments thereby permitting the cast to be separated into two separate halves.

* * * * *